US00PP32324P2

(12) United States Plant Patent
Hansen

(10) Patent No.: US PP32,324 P2
(45) Date of Patent: Oct. 13, 2020

(54) ***PHLOX* PLANT NAMED 'PARTY GIRL'**

(50) Latin Name: *Phlox paniculata*
Varietal Denomination: Party Girl

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 16/873,087

(22) Filed: Jan. 30, 2020

(51) Int. Cl.
*A01H 5/02* (2018.01)
*A01H 6/70* (2018.01)

(52) U.S. Cl.
USPC ..... Plt./320

(58) Field of Classification Search
USPC ..... Plt./320
See application file for complete search history.

*Primary Examiner* — Susan McCormick Ewoldt

(57) ABSTRACT

A new and unique hybrid cultivar of *Phlox* plant named *Phlox* 'Party Girl' of medium-height, multi-stemmed, upright habit. Foliage is thick, with good powdery mildew resistance on stiff stems. The new plant has near-white to pale-pink flowers with distinct darker pink eye-ring that are produced on large heads of branched peduncles and nearly cover the top of the plant beginning mid-July and continuing and reblooming for about six weeks through late summer. 'Party Girl' is especially suitable as a potted plant, for the garden, for attracting hummingbirds and butterflies, and for cut flower arrangements.

1 Drawing Sheet

Botanical classification: *Phlox paniculata.*
Variety denomination: 'Party Girl'.

STATEMENT REGARDING PRIOR DISCLOSURES UNDER 37 CFR 1.77(B)(6)

The first non-enabling disclosure, in the form of a website with a photograph and brief description was on Feb. 1, 2019 maintained by Walters Gardens, Inc. Subsequently, Walters Gardens, Inc. published an advertisement in their "Walters Gardens 19-20 Catalog" on May 29, 2019, and first sold the new plant on Jul. 8, 2019. Walters Gardens, Inc. obtained the new plant and all information relating thereto, from the inventor. No plants of *Phlox* 'Party Girl' have been sold, in this country or anywhere in the world, under this or any name, nor has any disclosure of the new plant been made more than one year prior the filing date of this application, and such sale or disclosure within one year was either derived directly or indirectly from the inventor.

BACKGROUND OF THE INVENTION

The present invention relates to a new and distinct hybrid Tall *Phlox* plant known as *Phlox* 'Party Girl' and will be referred to hereafter by its cultivar name or the "new plant". The new plant was the result of a controlled pollination of the proprietary, unreleased, hybrid known only as 2013 PHL-17-AA (not patented) as the female or seed parent and 'Grenadine Dream' U.S. Plant Pat. No. 19,183 as the male or pollen parent. The cross was performed by the inventor on Sep. 25, 2014 in the greenhouses at a wholesale perennial nursery in Zeeland, Mich., and seed was collected in the autumn of 2015. During the trial process the new plant arising as a single seedling selection from the identified cross was identified by the breeder code 14-648-1. 'Party Girl' has been asexually propagated by tip and basal stem cuttings in the greenhouses at the same nursery in Zeeland, Mich. since 2016, as well as by shoot tip tissue culture. The unique characteristics of the new plant have been found to be reproducible and stable in successive generations of asexually propagated plants and the resultant plants have been found to be identical to the original selection.

BRIEF SUMMARY OF THE PLANT

*Phlox* 'Party Girl' is unique from its parents and all other tall garden *Phlox* or other hybrid *Phlox* known to the inventor. The closest comparison cultivars known to the inventor are 'Ditosmel' U.S. Plant Pat. No. 20,593, 'Jordan Schuster' U.S. Plant Pat. No. 26,352, 'Swizzle' U.S. Plant Pat. No. 19,813, 'Thai Pink Jade' U.S. Plant Pat. No. 22,961 and 'Bright Eyes' (not patented). 'Ditosmel' is shorter in habit with smaller flower heads petals that faintly overlap and having a deeper pink coloration than the new plant. 'Jordan Schuster' has a deeper pink flower with narrow petals that do not overlap. 'Swizzle' has a much shorter habit, smaller flower heads and less overlapping of the petals. 'Thai Pink Jade' is taller in habit, the flower heads are fuller and the petals are lighter pink and more overlapping. The new plant may also be compared with 'Glamour Girl' U.S. Plant Pat. No. 25,778 which has a similar habit and plants size, but the flowers are hot coral pink. Copending U.S. Plant patent application Ser. No. 16/873,088 'Cover Girl' has a slightly taller habit and lavender-purple flowers. Copending U.S. Plant patent application Ser. No. 16/873,086 'Uptown Girl' has a slightly taller habit with flowers that are light pinkish lavender with a darker center. 'Grenadine Dream' has flowers that are much darker reddish-purple. 'Bright Eyes' has a taller habit, the petals are not as overlapping and the flower color is more light pink with a dark pink eye that is more gradually defused into the light pink background.

'Party Girl' differs from all other *Phlox* known to the inventor in the following repeatedly observed traits in combination:

1. Medium height plants of upright habit, producing clean, medium-green, lanceolate leaves;
2. Showing good powdery mildew resistance;
3. Multiple stems produce large branched mounds of flowers starting in mid-July for about six weeks;
4. Near-white to pale pink flowers with pink star-shaped center eye-ring on strong stiff stems;
5. Flowers cover nearly the entire top of the plant;

BRIEF DESCRIPTION OF THE DRAWINGS

The photographs of the new plant demonstrate the unique traits of 'Party Girl' and the overall appearance of three-year-old plants grown in a full sun trial garden in Zeeland, Mich. The colors are as accurate as reasonably possible with color reproductions. Variation in ambient light spectrum, source and direction may cause the appearance of minor variation in color.

DETAILED BOTANICAL DESCRIPTION

Figure 1:
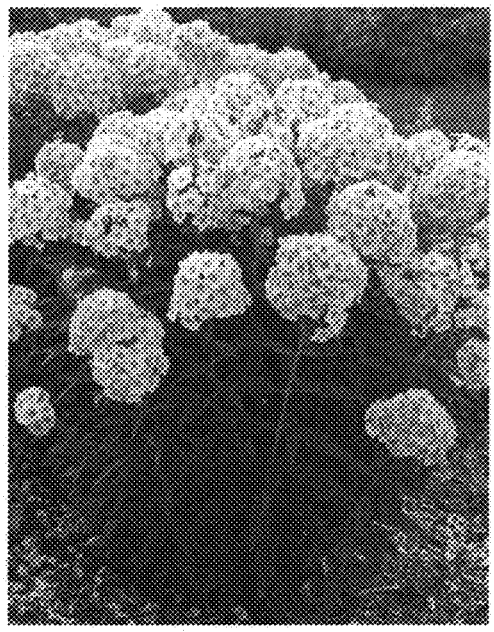
FIG. 1 shows the habit of the new plant in peak flower in the landscape.
Figure 2:
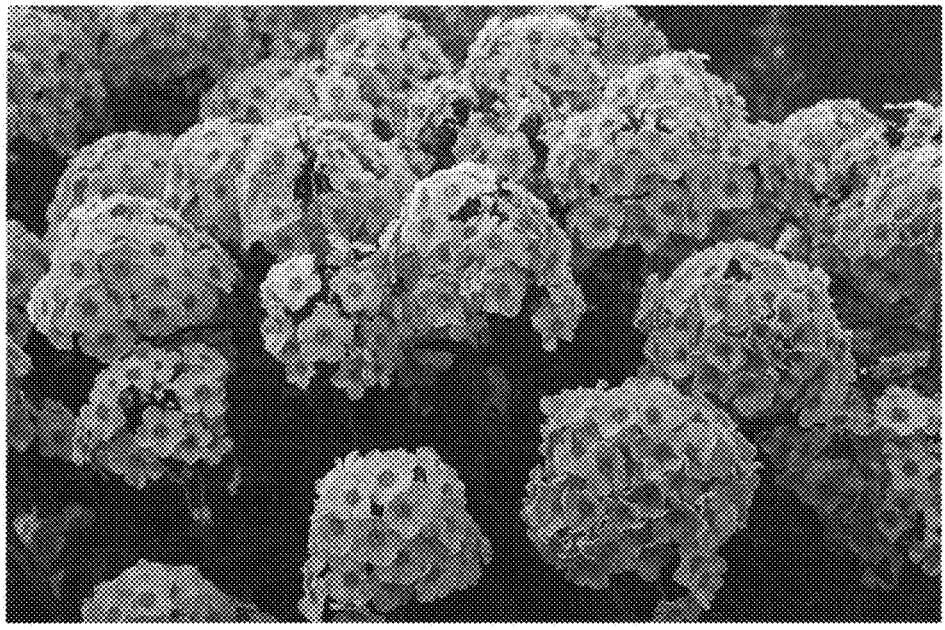
FIG. 2 shows a close-up of the floriferous flower head with flowers and buds.

The following descriptions and color references are based on the 2015 edition of The Royal Horticultural Society Colour Chart except where common dictionary terms are used. *Phlox* 'Party Girl' has not been observed under all possible environments. The phenotype may vary slightly with different growing environments such as temperature, light, fertility, soil pH, moisture and maturity levels, but without any change in the genotype. The following observations and size descriptions are based on three-year-old plants in the full sun garden of a wholesale perennial nursery in Zeeland, Mich. with supplemental fertilizer and water as needed.

Botanical classification: *Phlox paniculata;*

Parentage: 2013 PHL AA-2 as the female or seed parent and 'Grenadine Dream' as the male or pollen parent;

Plant habit: Hardy herbaceous perennial, densely upright, producing about 31 rigid mostly upright stems; flowering at up to 66.0 cm tall and about 60.0 cm wide; flowering begins mid-July in Michigan and continuing for about 6 weeks with repeating into late summer;

Propagation: Stem cuttings; rooting in about 21 days;

Time to produce finished crop in 3.8 liter pots: About 10 to 12 weeks from a 25 mm liner; moderate rate of growth;

Root: Primary roots to about 1.0 mm thick; secondary fibrous and freely branching; color creamy white to tan depending on soil type; color of active roots nearest RHS NN155B depending on soil components;

Leaves: Simple; opposite; ovoid; acute apex; rounded to truncate base; sessile; entire margin; tough, coriaceous; glabrous adaxial and abaxial;

Leaf size: To about 13.0 cm long by about 40.0 mm wide; average about 12.3 cm long by about 30.0 mm wide; becoming smaller distally;

Leaf surfaces: Glabrous and lustrous adaxial, glabrous and matte abaxial;

Leaf color expanding: Adaxial between RHS 138A and RHS 146B, abaxial nearest RHS 146B;

Leaf color at flowering: Adaxial between RHS NN137A and RHS 137A, abaxial between RHS 146B and RHS 138B;

Foliage fragrance: None detected;

Veins: Pinnate; glabrous adaxial and abaxial; midrib about 1.5 mm wide at base, slightly sunken adaxial and raised abaxial;

Vein color: Adaxial midrib nearest RHS 146D and lateral veins between RHS 146D and RHS 151D, abaxial midrib nearest RHS 145C and laterally nearest RHS 146D;

Petiole: Leaves sessile;

Stems: About 31 per plant; cylindrical; stiff; wiry; strong; mostly upright; glabrous; to about 66.0 cm long and 10 mm diameter at base, average about 58.0 cm long and 8.0 mm diameter at base;

Stem color: Nearest RHS 146D;

Nodes: About 13 per stem below initial flowers plus 12 nodes in branched flower head; average internode length about 2.6 cm;

Node color: Nearest RHS 146D;

Inflorescence: A loosely-branched compound corymb of about 120 flowers; flowering portion about 32.0 cm long and 17.0 cm across;

Flowers: Perfect; salverform with flat face and long fused tube; actinomophic; typically with five petals; about 28.0 mm long total with tube about 25.0 mm long and 2.5 mm diameter at base and 5.0 mm diameter below face; face about 25.0 mm across; attitude upright to slightly outward; self-cleaning;

Flower longevity: Individually about 5 days on plant or as cut flower;

Flower fragrance: Lightly sweet;

Buds one to two days prior to opening: Narrowly oblanceolate, to nearly clavate; acute apex with petals implicate about each other; base fused; total bud about 29.0 mm long, tube about 24.0 mm long and 2.5 mm diameter in tube base, bulb 9.0 mm long and swollen to 5.0 mm diameter toward apex of convolute petals;

Bud color: Petals nearest RHS N80C in bulb, and nearest RHS N77B in distal corolla tube, proximal tube nearest RHS 145D;

Petals: Five; sympetalous; margin entire; apex rounded; base fused into tube; abaxial and adaxial limb glabrous except distal 4 mm of abaxial corolla tube and adaxial corolla pubescent between 4 mm and 8 mm from base; limbs moderately imbricate, about 20 percent over the next petal;

Petal size: Limb to about 12.0 mm wide and about 11.0 mm long, corolla tube to about 25.0 mm long and 2.5 mm diameter at base and 5.0 mm diameter at face;

Petal color: Not fading with maturity; adaxial limb more white than RHS 69D with center eye band about 3.0 mm long and 1.5 mm wide nearest RHS 71D; abaxial limb distal portion between RHS 69D and RHS NN155D and proximal portion between RHS N75A and RHS 76B; adaxial corolla tube basal 2.0 mm nearest RHS 155A, distally between RHS 76A and RHS 76B; abaxial corolla tube basal 2.0 mm nearest RHS 155A, distally nearest RHS 77B;

Androecium: Five;

*Filaments.*—Typically five; straight; cylindrical; adnate to adaxial corolla tube except free in distal 1.0 mm; varying lengths between 14.0 mm and 18.0 mm, about 0.2 mm in diameter; color nearest RHS NN155D.

*Anther*.—Five; oblong elliptic; dorsifixed; longitudinal; about 4.0 mm long by 1.0 mm wide; color nearest RHS 11D.

*Pollen*.—Abundant; color nearest RHS 11C.

Gynoecium: One pistil per flower; to about 24.0 mm long;

*Style*.—Cylindrical; straight; about 20.5 mm long and about 0.3 mm diameter; persistent after flower abscission; color nearest RHS 143C.

*Stigma*.—Trifid in the distal 1.0 mm, about 0.3 mm in diameter; color nearest RHS 143D.

*Ovary*.—Superior; conical; acute apex, base truncate; about 2.5 mm long and 1.0 mm diameter; color nearest RHS 143A.

Calyx: Tubular; adpressed to corolla tube; to about 9.0 mm long and 3.5 mm cross at apex;

Sepals: Five; linear; narrowly acute apex, margin entire; basal 3.0 mm fused; abaxial surface matte and adaxial slightly lustrous; persistent; individually about 9.0 mm long and 1.0 mm wide;

Sepal color: Adaxial nearest RHS 146B with moderate blush nearest RHS 187B and 0.5 mm wide margin nearest RHS 161D; abaxial nearest RHS 146D with moderate blush nearest RHS 178B and 0.5 mm wide margin nearest RHS 161D;

Peduncle: Glabrous, stiff, strong, moderately lustrous, upright, cylindrical; flowering portion average about 28.0 cm long, and 4.0 mm diameter at base of flower branches; branches to about 16.0 mm long and 2.5 mm diameter at base;

Peduncle color: Nearest blend of RHS 145A and RHS 146D with strong blush of nearest RHS 187C in distal regions of high light intensity;

Bracts: Subtending upper branches and flowers; lanceolate; ciliolate margin; acute apex; sessile truncate base; glabrous; to about 4.0 cm long and 1.0 cm wide;

Bract color: Same as leaves in both adaxial and abaxial surfaces;

Pedicel: Cylindrical; micro-puberulent; about 3.0 mm long and 1.0 mm diameter;

Pedicel color: Nearest RHS 146C with moderate blush of nearest RHS 187B;

Fruit: 1 or 2 seeded; dehiscent septicidal capsule; about 7.0 mm long and 4.5 mm across; acute apex; truncate base; color as nearest RHS 166B;

Seeds: Typically 1 to 2 per capsule; ellipsoidal; about 4.5 mm long×3.0 mm wide and 1.0 mm thick; color nearest a blend between RHS 200A and RHS 202A;

Hardiness and culture: The new plant grows best with plenty of moisture and adequate drainage; hardy to at least from USDA zone 4 through 8.

Disease and pest resistance: *Phlox* 'Party Girl' demonstrated the excellent powdery mildew resistance caused by *Erysiphe cichoracearum* in the presence and under conditions of intense pressure that would normally show symptoms.

I claim:

1. A new and distinct cultivar of hybrid *Phlox* plant named *Phlox* 'Party Girl', as herein described and illustrated.

* * * * *